(12) United States Patent
Sahnoune et al.

(10) Patent No.: US 12,582,815 B2
(45) Date of Patent: Mar. 24, 2026

(54) ASSEMBLY COMPRISING A PORTABLE CENTRIFUGAL PUMP AND AN ELECTROMAGNETIC MOTOR

(71) Applicants: FONDATION HÔPITAL SAINT JOSEPH, Paris (FR); CENTRALESUPELEC, Gif-sur-Yvette (FR); CENTRE NATIONAL DE LA RECHERCHE SCIENTIFIQUE, Paris (FR); UNIVERSITE PARIS SACLAY, Gif-sur-Yvette (FR); SORBONNE UNIVERSITE, Paris (FR)

(72) Inventors: Abdelhakim Sahnoune, Antony (FR); Claude Marchand, Palaiseau (FR); Guillaume Krebs, Marcoussis (FR); Maya Hage-Hassan, Paris (FR)

(73) Assignees: FONDATION HÔPITAL SAINT JOSEPH, Paris (FR); CENTRALESUPELEC; CENTRE NATIONAL DE LA RECHERCHE SCIENTIFIQUE, Paris (FR); UNIVERSITE PARIS SACLAY, Gif-sur-Yvette (FR); SORBONNE UNIVERSITE, Paris (FR)

( * ) Notice: Subject to any disclaimer, the term of this patent is extended or adjusted under 35 U.S.C. 154(b) by 210 days.

(21) Appl. No.: 18/687,649

(22) PCT Filed: Aug. 26, 2022

(86) PCT No.: PCT/EP2022/073760
§ 371 (c)(1),
(2) Date: Feb. 28, 2024

(87) PCT Pub. No.: WO2023/031031
PCT Pub. Date: Mar. 9, 2023

(65) Prior Publication Data
US 2024/0382743 A1 Nov. 21, 2024

(30) Foreign Application Priority Data

Aug. 30, 2021 (FR) ....................................... 2109035

(51) Int. Cl.
*A61M 60/422* (2021.01)
*A61M 60/232* (2021.01)
(Continued)

(52) U.S. Cl.
CPC ........ *A61M 60/422* (2021.01); *A61M 60/232* (2021.01); *H02K 1/2766* (2013.01); *H02K 7/14* (2013.01); *F04D 13/06* (2013.01)

(58) Field of Classification Search
CPC .......... H02K 16/02; H02K 21/16; H02K 1/14; H02K 1/22; A61M 60/232; A61M 60/422
See application file for complete search history.

(56) References Cited

U.S. PATENT DOCUMENTS 6,181,040 B1 * 1/2001 Schob .................. A61M 60/113
310/90.5
2009/0001831 A1 * 1/2009 Cho ....................... H02K 21/16
29/598
(Continued)

FOREIGN PATENT DOCUMENTS

CN 107026547 A * 8/2017 ............. H02K 17/18
CN 113270970 A 8/2021
(Continued)

OTHER PUBLICATIONS

18687649_2025-11-05_CN_107026547_A_H.pdf (Year: 2025).*
(Continued)

*Primary Examiner* — Christopher M Koehler
*Assistant Examiner* — Ahmed F Seck
(74) *Attorney, Agent, or Firm* — Cushman Partners, LLC

(57) ABSTRACT

An assembly includes a portable centrifugal pump and an electromagnetic motor including a rotor having an axis X
(Continued)

and including first main permanent magnets that cooperate with a stator and are arranged in pairs, in particular in fours. The first main permanent magnets are arranged opposite a magnetised part that is capable of bearing the same number of magnets as the number of first permanent magnets and is secured to the pump. The first main permanent magnets create a magnetic flux. The magnetic flux of the rotor interacts with axial protruding poles and radial protruding poles of the stator.

10 Claims, 4 Drawing Sheets

(51) Int. Cl.
| | | |
|---|---|---|
| *F04D 13/06* | (2006.01) | |
| *H02K 1/276* | (2022.01) | |
| *H02K 7/14* | (2006.01) | |

(56) References Cited

U.S. PATENT DOCUMENTS

| | | | |
|---|---|---|---|
| 2010/0152524 A1 | 6/2010 | Sentmanat | |
| 2014/0030122 A1 | 1/2014 | Ozaki et al. | |
| 2020/0018318 A1 * | 1/2020 | Chen ................... | A61M 60/422 |

FOREIGN PATENT DOCUMENTS

| | | | | |
|---|---|---|---|---|
| WO | WO 00/64030 A1 | 10/2000 | | |
| WO | WO-2007139557 A1 * | 12/2007 | ............. | H02K 19/20 |
| WO | WO 2013/063661 A2 | 5/2013 | | |

OTHER PUBLICATIONS

18687649_2025-11-05_WO_2007139557_A1_H.pdf (Year: 2025).*
International Search Report as issued in International Patent Application No. PCT/EP2022/073760, dated Dec. 22, 2022.

* cited by examiner

[Fig. 1]
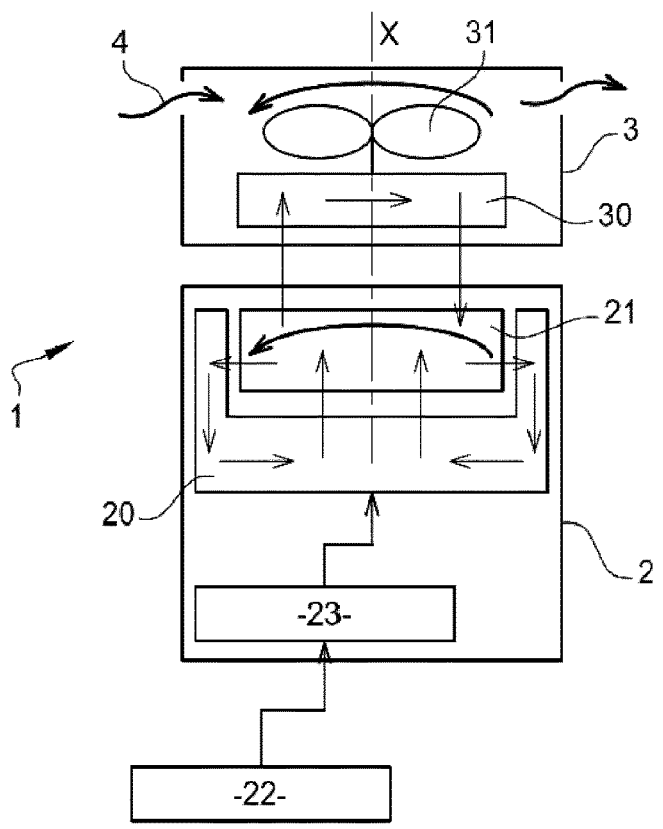
[Fig. 2]
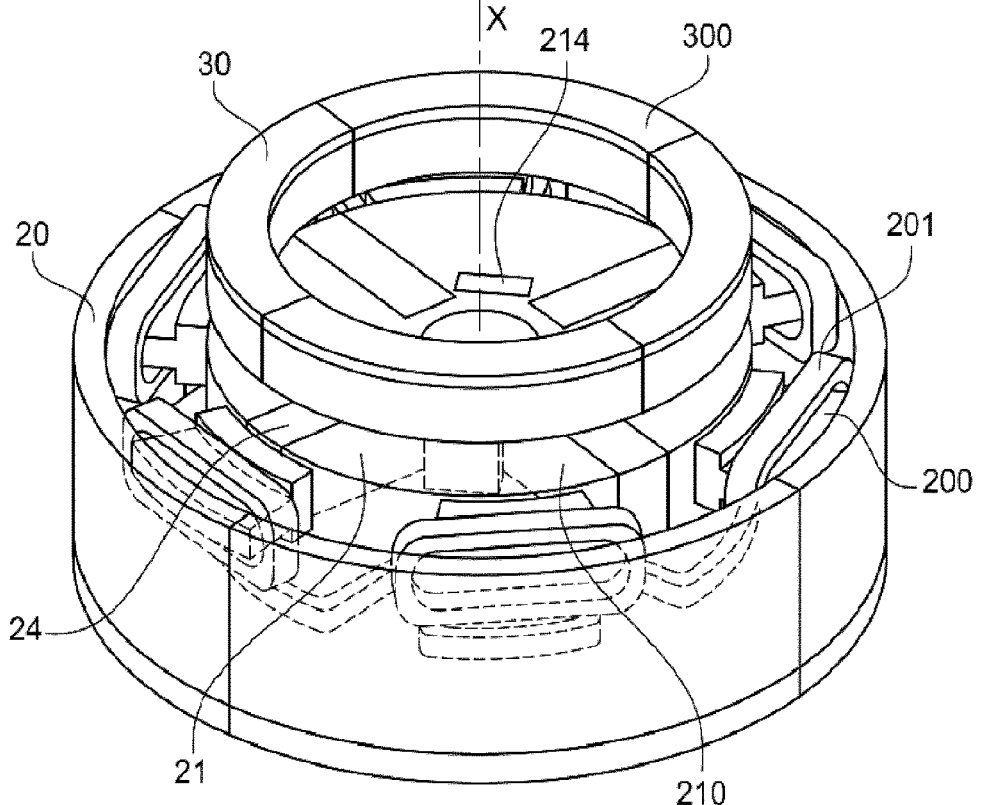

[Fig. 3]
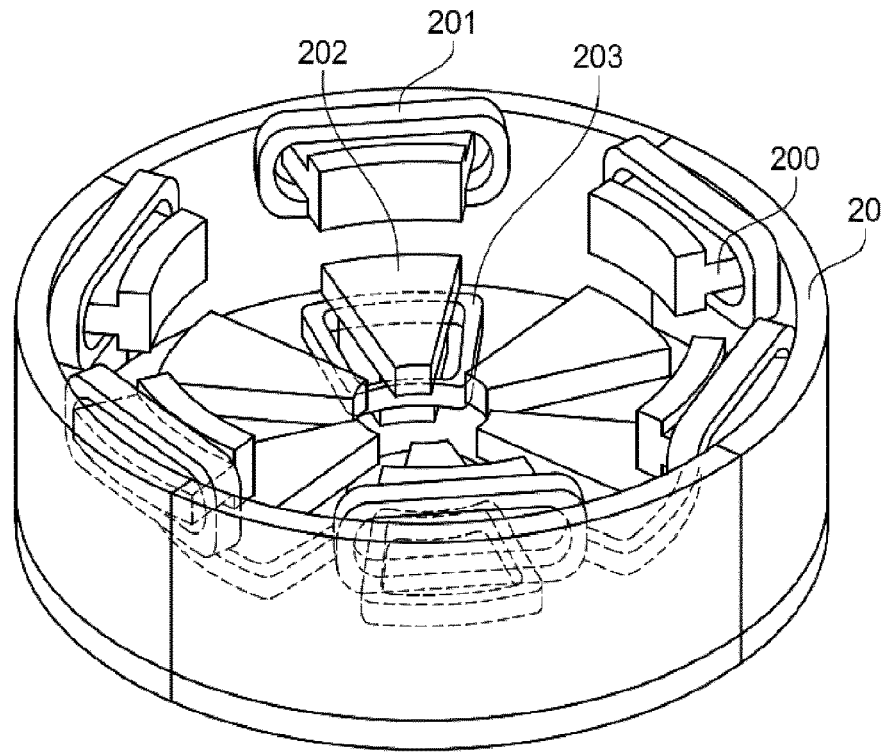
[Fig. 4]
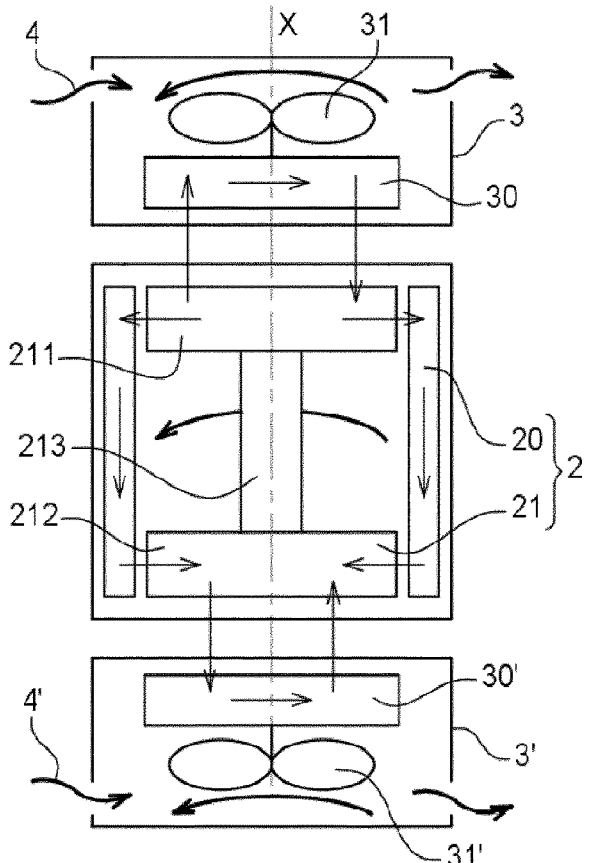

[Fig. 5]
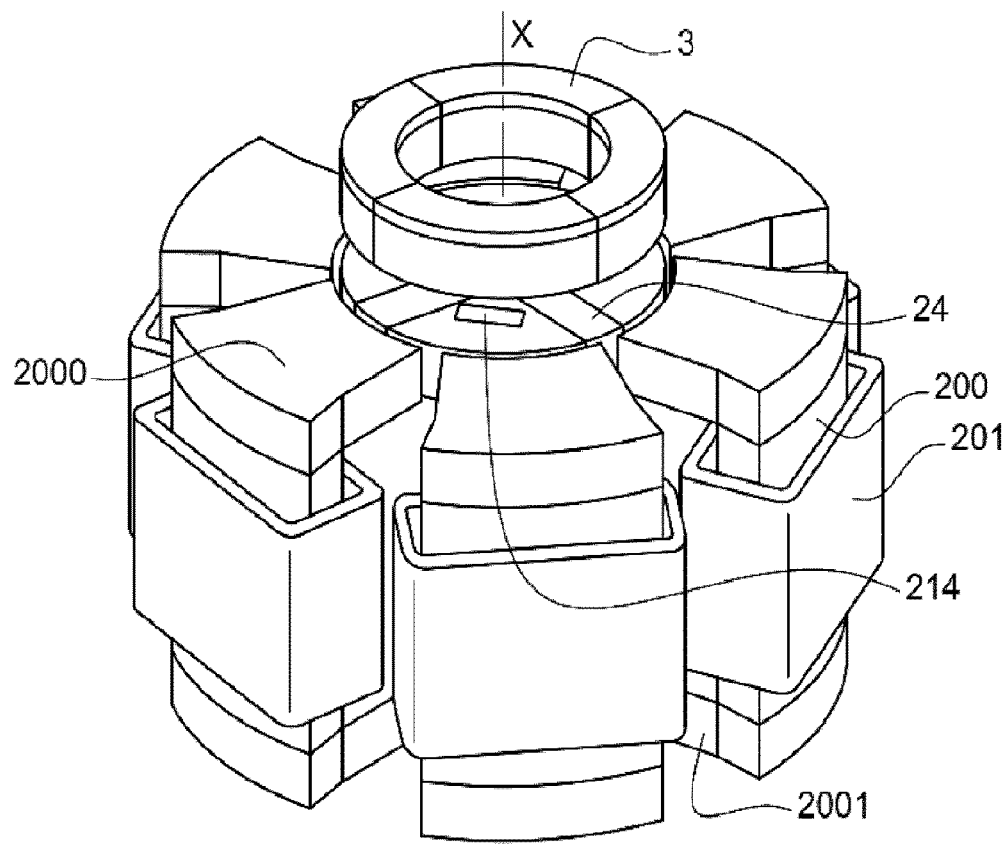
[Fig. 6]
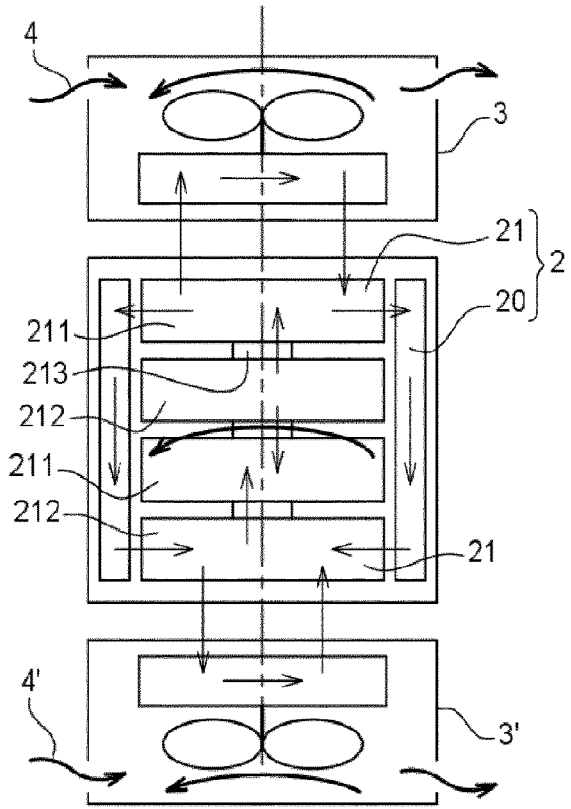

[Fig. 7]
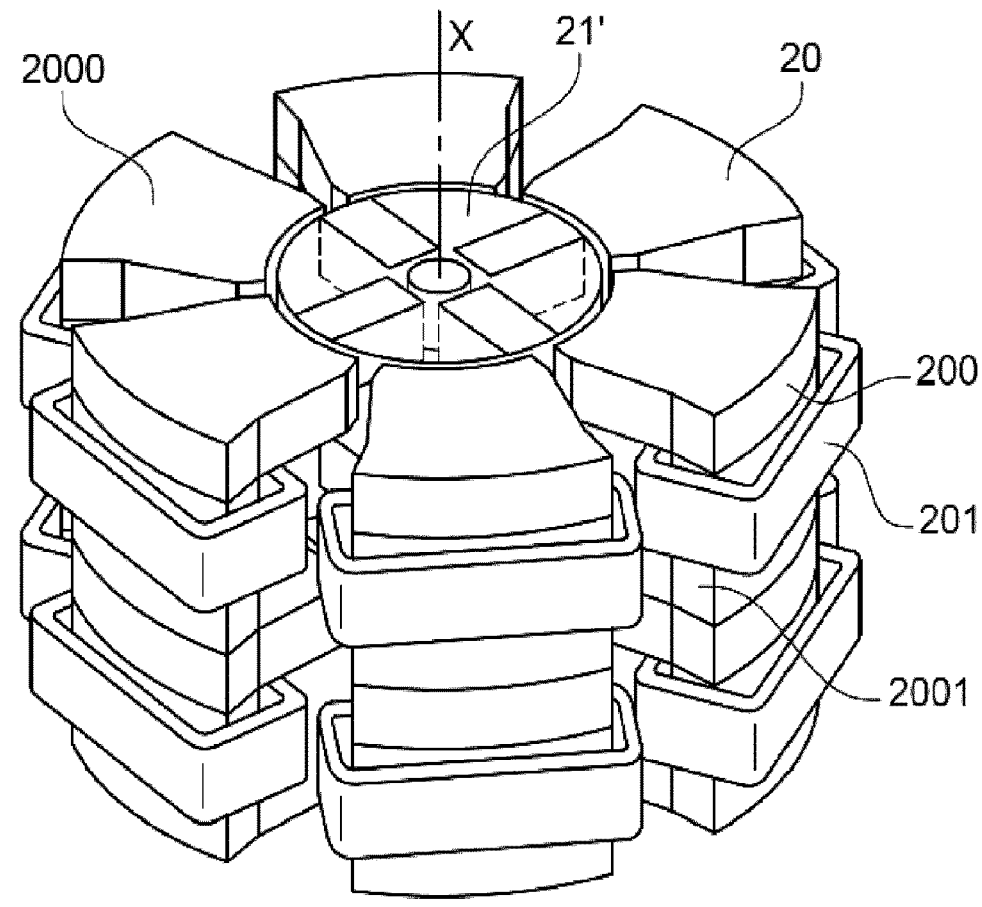
[Fig. 8]
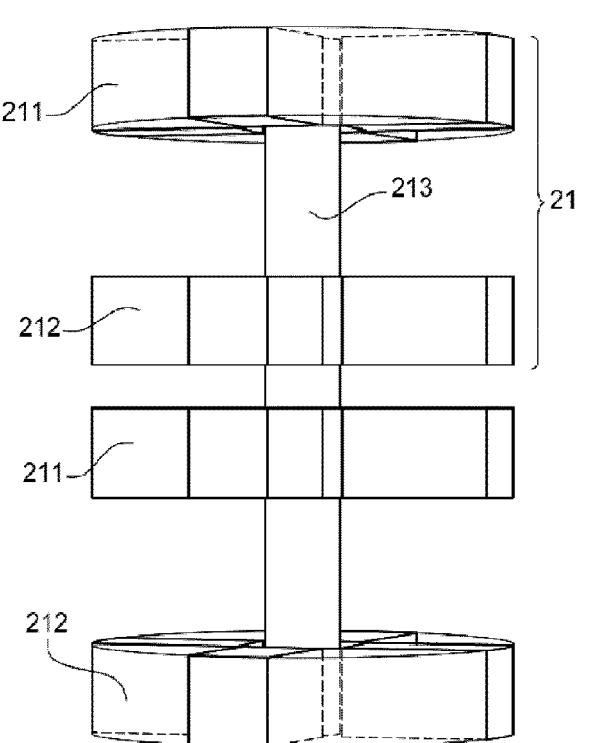

ASSEMBLY COMPRISING A PORTABLE CENTRIFUGAL PUMP AND AN ELECTROMAGNETIC MOTOR

CROSS-REFERENCE TO RELATED APPLICATIONS

This application is the U.S. National Stage of PCT/EP2022/073760, filed Aug. 26, 2022, which in turn claims priority to French patent application number 2109035 filed Aug. 30, 2021. The content of these applications are incorporated herein by reference in their entireties.

TECHNICAL FIELD OF THE INVENTION

The technical field of the invention is that of centrifugal pumps driven by an electromagnetic motor.

The present invention relates in particular to an assembly comprising a portable pump and an electromagnetic motor.

TECHNOLOGICAL BACKGROUND OF THE INVENTION

These types of assembly are especially used in the medical field for circulating a liquid product, such as blood for example, in the event of heart or respiratory failure. The pumps have an impeller connected to a pump rotor which is driven by a drive rotor provided with a rotor disc, this drive rotor and this rotor disc being equipped with drive permanent magnets. Permanent magnets located on the pump rotor are associated with the drive permanent magnets to create magnetic coupling, and with the magnetising coils of a stator of the drive device, to produce rotational movement.

However, these pumps are often of large overall size because they require an axial flux and their efficiency is limited to between 5 and 15%. The axial flux is created by specific magnets or by the electric motor when the latter is of an axial flux.

The use of specific magnets to create the axial flux increases inertia of the assembly and therefore its efficiency, but also its dimensions.

The axial flux electric motor is more complex to make, more difficult to cool and has a larger diameter than a radial flux motor.

There are also radial flux assemblies where the pump is driven by a shaft placed facing the rotor of the motor. However, this solution is not satisfactory because it requires an additional piece which makes the assembly heavier and reduces efficiency.

SUMMARY OF THE INVENTION

The invention offers a solution to the previously discussed problems, by making it possible to use an assembly that is both more efficient and of less overall size.

The assembly according to the invention comprises a portable centrifugal pump and an electromagnetic motor consisting of a rotor of axis X comprising first permanent magnets cooperating with a stator and arranged in pairs, it is characterised in that the first permanent magnets are facing a magnetised piece integral with the pump and in that the first permanent magnets are in an axial magnetic flux which with axial poles and in radial magnetic flux with radial poles. The use of permanent magnets in a configuration of axial and radial, that is three-dimensional, magnetic flux circulation makes it possible to have both a smaller diameter and a lower height since it is not necessary to provide a second set of magnets, the magnetic coupling being achieved by direct interaction of the rotating magnetised part of the pump with the magnetic poles of the rotor of the motor. Indeed, the arrangement of the first magnets, the pole pieces and the stator enables creation of both an axial and radial magnetic flux.

The assembly is therefore smaller, lighter and more efficient, thereby especially enabling easier implantation. As there are fewer rotating pieces, the on-board mass is lower, resulting in lower inertia and the possibility of angular acceleration. There is also a better robustness of the pump.

Advantageously, the centrifugal pump is dismountable from the electromagnetic motor. It is therefore possible to dismount the pump and replace it while keeping the same motor, which avoids having to replace the pump+motor assembly, particularly in medical use where the pump has to be changed for each user.

Advantageously, the rotor comprises second permanent magnets. These magnets interact with the first magnets of the rotor.

Advantageously, the second permanent magnets are arranged in pairs.

Advantageously, the number of second permanent magnets is the same as the number of first permanent magnets. The first and second magnets can thus interact in an optimised manner.

According to a first alternative, the rotor comprises two discs connected through a shaft of axis X, the stator has salient poles, each salient pole is U-shaped with two legs at each axial end directed towards the rotor, each leg radially facing one of the discs and the assembly comprises the pump placed axially facing one of the two discs and another pump is placed axially on the opposite side to the first pump facing the other disc. The same motor thus drives two pumps, which is particularly interesting for portable medical pumps which can then have a higher flow rate and greater reliability by virtue of the redundancy.

According to a second alternative, the rotor comprises several discs connected through a shaft of axis X, the stator consists of several stator elements with salient poles stacked on top of each other, each salient pole is U-shaped with two legs directed towards the rotor at each axial end, each leg being radially facing one of the discs and the assembly comprises the pump arranged axially facing one of the discs placed at one axial end and another pump arranged axially facing another disc placed at the other axial end. The stack of stator elements makes it possible to obtain greater torque. Permanent magnets are placed within the rotors (of ferromagnetic material) and oriented in a specific manner in order to achieve flux concentration in the air gap. Fluxes captured by the stator coils can then be sinusoidal or trapezoidal.

Advantageously, the assembly has a diameter of between 10 and 160 mm. This diameter enables the pump and its motor to be implanted close to a vein or artery.

Advantageously, the assembly has a length of between 32 and 85 mm. The overall size is thus limited.

According to one particular arrangement, the pump is a medical pump.

The invention and its different applications will be better understood upon reading the following description and upon examining the accompanying figures.

BRIEF DESCRIPTION OF THE FIGURES

The figures are set forth by way of indicating and in no way limiting purposes of the invention.

FIG. 1 is a schematic representation of a first embodiment of the assembly according to the invention;

FIG. 2 is a perspective view of an assembly of FIG. 1;

FIG. 3 is a view of the stator of FIG. 2;

FIG. 4 is a schematic representation of a second embodiment of the assembly according to the invention;

FIG. 5 is a perspective view of an assembly of FIG. 4;

FIG. 6 is a schematic representation of a third embodiment of the assembly according to the invention;

FIG. 7 is a perspective view of an assembly of FIG. 6;

FIG. 8 is a view of the rotor of FIG. 7.

DETAILED DESCRIPTION

Unless otherwise specified, a same element appearing in different figures has a single reference.

As can be seen in FIG. 1, the assembly 1 comprises a motor 2 and a portable centrifugal pump 3. The pump 3 comprises a magnetised piece 30 integral with fins 31 allowing circulation 4 of a liquid product such as blood, for example. The motor 2 comprises a rotor 21 and a stator 20 of axis X, and is powered by a battery 22 or an electrical energy source with an inverter and an associated controller 23. The rotor 21 directly interacts not only with the stator 20 but also with the magnetised piece 30. The assembly 1 rotates about axis X. The rotor 21 may comprise a shaft made of aluminium or non-magnetic material.

The stator 20 is of ferromagnetic material (e.g. iron) and comprises several radially arranged salient poles 200 and axially arranged salient poles 202, each with a winding 201 and 203 respectively, as shown in FIG. 3. The windings 201 and 203 may be of copper. The coils preferably form a polyphase electrical system, so the system can comprise more than three phases, thereby improving reconfiguration possibilities.

The axial poles 202 contribute to the creation of axial flux, the flux leaving the magnets will be captured by the poles 200 (creation of the radial flux) and the poles 202 (creation of the axial flux). The poles 200+202 will therefore create a three-dimensional radial and axial flux. They could also ensure levitation of the rotor when there is no mechanical shaft, the machine having two (radial and axial) air gaps.

The rotor 21 is shaped as a disc 210 comprising pairs of first permanent magnets 24, two pairs in FIG. 2. These first magnets 24 are facing the salient poles 200 and 202 of the stator 20 and the magnetised piece 30. In the example of FIG. 2, the magnetised piece 30 comprises four magnetised sectors 300. The rotor 21 may also comprise second permanent magnets 214 arranged in a ferromagnetic material between two first magnets 24 and oriented in a plane tangential to the surface of the rotor 21. These second magnets 214 allow increase in the flux and torque.

In the second embodiment illustrated in FIGS. 4 and 5, the assembly comprises two identical pumps 3 and 3', each with a magnetised piece 30 and 30', arranged axially on either side of the motor 2 in order to keep the motor balanced. The use of two identical pumps makes it possible to circulate two liquids 4 and 4' separately to ensure redundancy or a higher flow rate.

The rotor 21 of motor 2 comprises two discs 211 and 212 connected through a shaft 213 of axis X. The discs 211 and 212 are similar to the disc 210. The stator 20 has salient poles 200, U-shaped with each leg 2000 and 2001 being radially directed towards the rotor 21. A casing made of composite materials or plastic, for example, is provided to support the poles. A winding 201 is wound around the base of the U of each salient pole 200. The stator 20 comprises a casing made of non-magnetic material.

Each first magnet 24 of the rotor 21 magnetically attracts the magnetised piece 30 when the stator 20 is not powered. When the coils 201 are powered, the level of force can be adjusted by means of the motor control (equivalent to an internal angle adjustment). For optimum electromagnetic behaviour of the motor, the magnets are in the buried position. The number of poles on rotor 21 and the number of poles on magnet 30 can be different. A "V" arrangement of the first magnets 24 ensures concentration of magnetic flux in the air gap (and therefore more torque) but also three-dimensional circulation of the flux.

In the third embodiment visible in FIGS. 6, 7 and 8, there are two pumps 3 and 3' and a motor 2 as for the second embodiment. However, the motor 2 consists of a stack (here two) of stators 20 and rotors 21 similar to that of the second embodiment. The stators 20 are stacked on top of each other by the legs 2000 and 2001 of the salient poles 200 and the rotors 21 each comprise two discs 211 and 212 at the axial ends and connected together through a single shaft 213.

It is possible to stack more stators 20 and rotors 21 if greater torque is desired.

By virtue of the invention, it is possible to operate the pump in pulsed mode, in a manner analogous to the physiology of systemic blood circulation.

In the medical context, several therapeutic applications are contemplatable. The first is the use of this assembly within a transportable extracorporeal artificial lung. Other applications are possible, such as temporary assisted circulation for cardiogenic shock of the portable veno-arterial ECMO (ExtraCorporeal Membrane Oxygenation) type, by virtue of the miniaturisation of the motor, which makes it easier to get the patient upright and to resume walking, provided there are vascular accesses other than the femoral vessels (jugulo-axillary cannulation, for example). This miniaturisation can also be applied to mobile assisted circulation, facilitating the transport (by road and by air) of patients undergoing ECMO. Finally, the ability to generate a pulsed flux by optimising the torque improves biocompatibility of ECMO systems and can be applied in veno-arterial ECMO for refractory cardiogenic shock requiring more than one week's assistance (especially patients awaiting heart transplants). This latter indication could be the subject of preclinical and clinical research to study effects of pulsed physiology on the functional recovery kinetics of organs (kidney, liver, heart) and also on the occurrence of haemorrhagic events under ECMO (platelet consumption, circulating Willebrand factor concentration).

The invention claimed is:

1. An assembly comprising a portable centrifugal pump and an electromagnetic motor consisting of a rotor of axis X comprising first permanent magnets cooperating with a stator and arranged in pairs, wherein the first permanent magnets are facing a magnetised piece integral with the pump, wherein the stator comprises several radially arranged salient poles and axially arranged salient poles, each with a winding respectively, and wherein the first permanent magnets are in an axial magnetic flux with axial poles and in a radial magnetic flux with radial poles.

2. The assembly according to claim 1, wherein the centrifugal pump is dismountable from the electromagnetic motor.

3. The assembly according to claim 1, wherein the rotor comprises second permanent magnets.

4. The assembly according to claim 3, wherein the second permanent magnets are arranged in pairs.

5. The assembly according to claim 3, wherein a number of second permanent magnets is identical to a number of first permanent magnets.

6. The assembly according to claim 1, wherein the assembly has a diameter of between 10 and 160 mm.

7. The assembly according to claim 1, wherein the assembly has a length of between 32 and 85 mm.

8. The assembly according to claim 1, wherein the pump is a medical pump.

9. An assembly comprising a portable centrifugal pump and an electromagnetic motor consisting of a rotor of axis X comprising first permanent magnets cooperating with a stator and arranged in pairs, wherein the rotor comprises two discs connected through a shaft of axis X, wherein the stator has salient poles, wherein each salient pole is U-shaped with two legs at each axial end directed towards the rotor, each leg being radially facing one of the discs and wherein the pump is placed axially facing one of the two discs and wherein another pump is disposed axially on the opposite side to the pump facing the other disc.

10. An assembly comprising a portable centrifugal pump and an electromagnetic motor consisting of a rotor of axis X comprising first permanent magnets cooperating with a stator and arranged in pairs, wherein the rotor comprises several discs connected through a shaft of axis X, wherein the stator consists of several stator elements with salient poles stacked on top of each other, wherein each salient pole is U-shaped with two legs directed towards the rotor at each axial end, each leg being radially facing one of the discs, wherein the pump is arranged axially facing one of the discs placed at one axial end and wherein another pump is arranged axially facing another disc placed at the other axial end.

* * * * *